US010758872B2

(12) United States Patent
Belfort et al.

(10) Patent No.: US 10,758,872 B2
(45) Date of Patent: Sep. 1, 2020

(54) SYNTHETIC MEMBRANES AND METHODS OF USE THEREOF

(71) Applicant: RENSSELAER POLYTECHNIC INSTITUTE, Troy, NY (US)

(72) Inventors: Georges Belfort, Slingerlands, NY (US); Joseph Grimaldi, Clifton Park, NY (US); Joseph Imbrogno, Massapequa, NY (US); James Kilduff, Saratoga Springs, NY (US); John Joseph Keating, Troy, NY (US)

(73) Assignee: Rensselaer Polytechnic Institute, Troy, MI (US)

( * ) Notice: Subject to any disclaimer, the term of this patent is extended or adjusted under 35 U.S.C. 154(b) by 0 days.

(21) Appl. No.: 16/733,810

(22) Filed: Jan. 3, 2020

(65) Prior Publication Data

US 2020/0139308 A1    May 7, 2020

Related U.S. Application Data

(63) Continuation of application No. 16/180,322, filed on Nov. 5, 2018, now abandoned, which is a continuation of application No. 15/593,675, filed on May 12, 2017, now Pat. No. 10,118,134, which is a continuation-in-part of application No. PCT/US2015/060899, filed on Nov. 16, 2015.

(60) Provisional application No. 62/079,605, filed on Nov. 14, 2014.

(51) Int. Cl.
| | | |
|---|---|---|
| *B01D 69/00* | (2006.01) | |
| *B01D 53/00* | (2006.01) | |
| *B01D 61/00* | (2006.01) | |
| *B01D 69/12* | (2006.01) | |
| *C07C 29/86* | (2006.01) | |
| *C02F 1/44* | (2006.01) | |
| *B01D 71/78* | (2006.01) | |
| *B01D 67/00* | (2006.01) | |
| *B01D 61/02* | (2006.01) | |
| *B01D 53/22* | (2006.01) | |
| *B01D 71/68* | (2006.01) | |
| *B01D 71/40* | (2006.01) | |
| *B01D 69/10* | (2006.01) | |
| *B01D 69/02* | (2006.01) | |
| *B01D 61/36* | (2006.01) | |
| *C02F 103/08* | (2006.01) | |
| *B01D 71/52* | (2006.01) | |
| *B01D 71/28* | (2006.01) | |

(52) U.S. Cl.
CPC ......... *B01D 69/125* (2013.01); *B01D 53/228* (2013.01); *B01D 61/025* (2013.01); *B01D 61/362* (2013.01); *B01D 67/0006* (2013.01); *B01D 67/0093* (2013.01); *B01D 69/02* (2013.01); *B01D 69/10* (2013.01); *B01D 69/12* (2013.01); *B01D 71/40* (2013.01); *B01D 71/68* (2013.01); *B01D 71/78* (2013.01); *C02F 1/441* (2013.01); *C07C 29/86* (2013.01); *B01D 61/02* (2013.01); *B01D 71/28* (2013.01); *B01D 71/52* (2013.01); *B01D 2257/708* (2013.01); *B01D 2323/08* (2013.01); *B01D 2323/34* (2013.01); *B01D 2323/345* (2013.01); *B01D 2323/38* (2013.01); *B01D 2323/385* (2013.01); *B01D 2325/02* (2013.01); *B01D 2325/26* (2013.01); *B01D 2325/38* (2013.01); *C02F 2103/08* (2013.01); *Y02A 50/235* (2018.01)

(58) Field of Classification Search
CPC ... B01D 69/125; B01D 53/228; B01D 61/025
See application file for complete search history.

(56) References Cited

U.S. PATENT DOCUMENTS

| | | | | |
|---|---|---|---|---|
| 3,953,566 A | * | 4/1976 | Gore | B01D 71/36 264/505 |
| 4,187,390 A | * | 2/1980 | Gore | B01D 71/36 174/102 R |
| 4,194,041 A | * | 3/1980 | Gore | B32B 5/18 442/289 |
| 4,608,060 A | * | 8/1986 | Kulprathipanja | B01D 67/0002 95/47 |

(Continued)

FOREIGN PATENT DOCUMENTS

WO    WO-2008106323 A2 * 9/2008 ............. B01D 65/10

*Primary Examiner* — Sikarl A Witherspoon
(74) *Attorney, Agent, or Firm* — Murtha Cullina LLP; Anthony P. Gangemi

(57) ABSTRACT

The present invention relates to synthetic membranes and use of these synthetic membranes for isolation of volatile organic compounds and purification of water. The synthetic membrane includes a hydrophobic polymer layer located on a polymeric membrane support layer. The invention includes a method of isolating volatile organic compounds with the synthetic membrane by contacting a volatile organic mixture with the hydrophobic polymer layer of the synthetic membrane and removing volatile organic compounds from the polymeric membrane support layer of the synthetic membrane by a process of pervaporation. The invention also includes a method of purifying water with the synthetic membrane by contacting an ionic solution with the hydrophobic polymer layer of the synthetic membrane and removing water from the polymeric membrane support layer of the synthetic membrane by a process of reverse osmosis. The invention also relates to methods of isolating non-polar gases by gas fractionation.

9 Claims, 7 Drawing Sheets

(56) References Cited

U.S. PATENT DOCUMENTS

| | | | | |
|---|---|---|---|---|
| 5,468,390 A | * | 11/1995 | Crivello | B01D 67/0093 |
| | | | | 210/490 |
| 5,852,127 A | * | 12/1998 | Belfort | B82Y 30/00 |
| | | | | 525/327.7 |
| 6,852,769 B2 | * | 2/2005 | Belfort | B01D 67/0093 |
| | | | | 210/490 |
| 7,604,746 B2 | * | 10/2009 | Childs | B01D 61/362 |
| | | | | 210/490 |
| 8,444,076 B2 | * | 5/2013 | Rukavina | B01F 7/0025 |
| | | | | 241/282.1 |
| 8,445,076 B2 | * | 5/2013 | Cohen | B01D 65/08 |
| | | | | 427/569 |
| 9,144,824 B2 | * | 9/2015 | Cohen | B05D 1/62 |

* cited by examiner

A.

B.

C.

SYNTHETIC MEMBRANES AND METHODS OF USE THEREOF

CROSS-REFERENCE TO RELATED APPLICATIONS

This application is a continuation of Ser. No. 16/180,322, filed Nov. 5, 2018, which is a continuation of Ser. No. 15/593,675, filed May 12, 2017, which is a Continuation-In-Part application of International Patent Application Serial No. PCT/US2015/060899, filed Nov. 16, 2015, which published on May 19, 2016 as International Publication No. WO 2016/077827 A1, and which claims priority under 35 U.S.C. § 119(e) to U.S. Provisional Patent Application Ser. No. 62/079,605, filed on Nov. 14, 2014, each of which is hereby incorporated by reference herein in its entirety.

STATEMENT ON FEDERALLY SPONSORED RESEARCH OR DEVELOPMENT

This invention was made with government support under grant numbers DE-FG02-09ER16005 and DE/SC0006520 awarded by the U.S. Department of Energy. The government has certain rights in the invention.

FIELD OF THE INVENTION

This invention relates to synthetic membranes and use of synthetic membranes in methods of isolation of volatile organic compounds and purification of water. The synthetic membrane includes a hydrophobic polymer layer located on a polymeric membrane support layer, wherein the hydrophobic polymer layer includes a plurality of polymer units covalently bonded to the polymeric membrane support layer, wherein each polymer unit includes a polymerized plurality of vinyl monomers. The synthetic membrane can be used in such isolation methods as pervaporation and reverse osmosis. The invention also relates to methods of isolating non-polar gases by gas fractionation.

BACKGROUND OF THE INVENTION

Pressure-driven membrane filtration processes have matured and are now widely accepted in many industries such as in energy, biotechnology, food and beverage, chemical, wastewater, gas fractionation, and desalination due to their low energy requirements and one-phase operation. Although membranes made from metals or ceramics are available, polymeric materials predominate (Ulbricht, Advanced Functional Polymer Membranes, Polymer, 2006, 47 (7), 2217-2262). For over 40 years, both interfacial polymerization (Cadotte et al., Thin-Film Composite RO Membranes: Origin, Development and Recent Advances, In Synthetic Membranes; Turbak, Ed., ACS Symposium Series, American Chemical Society. Washington, D.C., 1981; Vol. 1, pp 305-326) and phase inversion (Loeb, The Loeb-Sourirajan Membrane: How It Came About, in Synthetic Membranes, Turbak, Ed.; ACS Symposium Series, American Chemical Society: Washington, D.C., 1981; Vol. 1, pp 1-9) have been the predominant methods for preparing composite polymeric and asymmetric membrane structures, respectively. Although these synthesis methods have been very successful, they are both relatively complex and sensitive to small changes in the casting conditions (Elimelech et al., The future of seawater desalination: Energy, technology, and the environment, Science, 2011, 333 (6043), 712). Many research groups have sought novel synthesis methods for producing synthetic membranes without much success. These membranes suffer from limitations including low porosity (track etched) (Price et al., Observation of Charged Particle Tracks in Solids, J. Appl. Phys., 1962, 33, 3400; Price et al., Chemical Etching of Charged Particle Tracks, J. Appl. Phys. 1962, 33, 3407; Quinn et al., Model Pores of Molecular Dimension: The Preparation and Characterization of Track-Etched Membranes, Biophys. J., 1972, 12 (8), 990-1007), high cost (ceramic or stainless steel) (Anderson et al., Titania and Alumina Ceramic Membranes, J. Membr. Sci., 1988, 39 (3), 243-258), wide pore size distribution (stretched PTFE) (Gore et al., Process for producing porous products, U.S. Pat. No. 3,953,566; Gore et al., Waterproof laminate, U.S. Pat. No. 4,194,041; Gore, Porous products and process therefor. U.S. Pat. No. 4,187,390), and low strength (biological) (Renkin, Filtration, Diffusion, and Molecular Sieving Through Porous Cellulose Membranes, J. Gen. Physiol., 1954, 38 (2), 225-243), or are difficult to scale-up (zeolite, carbon-nanotubes or graphene oxide) (Yoo et al., High-Performance Randomly Oriented Zeolite Membranes Using Brittle Seeds and Rapid Thermal Processing, Angew. Chem., Int. Ed., 2010, 49 (46), 8699-8703; Hinds et al., Aligned multiwalled carbon nanotube membranes, Science, 2004, 303 (5654), 62-65, Nair et al., Unimpeded permeation of water through helium-leak-tight graphene-based membranes, Science, 2012, 335 (6067), 442-444).

We developed a new class of synthetic brush hydrophobic polymer membranes, and tested them with a challenging separation: removal of isobutanol from water by pervaporation (PV). To prepare the best performing hydrophobic brush membranes for this separation, we used our unique high throughput platform with 96 filter well plates (Zhou et al., High-throughput membrane surface modification to control NOM fouling, Environ. Sci. Technol., 2009, 43 (10), 3865-71). The method of preparation involves grafting commercially available vinyl monomers alone or in mixtures to light-sensitive poly(ether sulfone) (PES) nanofiltration membranes, screening for the best performers, and selecting the winners (Zhou et al., High Throughput Synthesis and Screening of New Protein Resistant Surfaces for Membrane Filtration, AIChE J., 2010, 56 (7), 1932-1945; Gu et al., High Throughput Atmospheric Pressure Plasma-Induced Graft Polymerization for Identifying Protein-Resistant Surfaces, Biomaterials, 2012, 33 (5), 1261-1270; Zhou et al., High Throughput Discovery of New Fouling-Resistant Surfaces, J. Mater. Chem., 2011, 21 (3), 693-704). The high throughput platform has also been used with combinatorial chemistry to generate a library of new monomers (Gu et al., High Throughput Atmospheric Pressure Plasma-Induced Graft Polymerization for Identifying Protein-Resistant Surfaces, Biomaterials, 2012, 33 (5), 1261-1270; Imbrogno et al., A New Combinatorial Method to Synthesize, Screen, and Discover Anti-Fouling Surface Chemistry, ACS Appl. Mater. Interfaces, 2015, 7, 2385-2392). The newly synthesized hydrophobic-terminated monomers were then grafted and polymerized on the surface of multiple light-sensitive PES membranes located in filter wells in 96 well plates. This high throughput process allows one to rapidly screen many different surface chemistries with reproducibility and high confidence. The selected winners were determined by measuring performance parameters: fouling index, selectivity, and permeation flux (inverse resistance to flow). This method allows one to fine-tune the surface chemistry based on the desired application.

Research on hydrophilic polymer brushes grafted inside of the pores of selective porous supports for pervaporation began in the 1990s (Ulbricht et al., Novel high performance photograft composite membranes for separation of organic liquids by pervaporation, J. Membr. Sci., 1997, 136 (1), 25-33; Yamaguchi et al., Plasma-graft filling polymerization: preparation of a new type of pervaporation membrane for organic liquid mixtures, Macromolecules, 1991, 24 (20), 5522-5527). More recently, non-hydrophobic polymer brush membranes on inorganic supports, first reported by Cohen's group 15 years ago, did not gain traction because they were difficult to prepare and scale-up, and the inorganic substrates were costly (Jou et al., A novel ceramic-supported polymer membrane for pervaporation of dilute volatile organic compounds, J. Membr. Sci., 1999, 162 (1), 269-284; Lin et al., Polymer surface nano-structuring of reverse osmosis membranes for fouling resistance and improved flux performance, J. Mater. Chem., 2010, 20 (22), 4642-4652; Yoshida et al., Ceramic-supported polymer membranes for pervaporation of binary organic/organic mixtures, J. Membr. Sci., 2003, 213 (1), 145-157). Specifically, relatively polar polyvinyl acetate polymer was grafted on inorganic silica membranes using a complicated three-step process and used for pervaporation of chlorinated hydrocarbons, such as chloroform and trichloroethylene from water (Jou et al., A novel ceramic-supported polymer membrane for pervaporation of dilute volatile organic compounds, J. Membr. Sci., 1999, 162 (1), 269-284). The differences between the polymer brush membranes prepared on inorganic supports and our new hydrophobic polymer brush membranes are significant, since our method requires less time (1 day vs 4-5 days), does not require harsh solvents or initiating catalysts, lacks complicated chemical modification steps, and uses hydrophobic brushes instead of hydrophilic brushes (Crivello et al., Low fouling ultrafiltration and microfiltration aryl polysulfone. U.S. Pat. No. 5,468,390). Our process is also scalable and less expensive (Zhou et al., High Throughput Synthesis and Screening of New Protein Resistant Surfaces for Membrane Filtration, AIChE J., 2010, 56 (7), 1932-1945; Zhou et al., High Throughput Discovery of New Fouling-Resistant Surfaces, J. Mater. Chem., 2011, 21 (3), 693-704; Taniguchi et al., Photo-processing and cleaning of PES and PSF Membranes, WO 03/078506; Belfort et al., UV-Assisted Grafting of PES and PSF Membranes, CA 2,422,738). Much of the focus since then has been on using grafted hydrophilic brushes to repel proteins and other molecules as an antifouling mitigation strategy (Lin et al., Polymer surface nano-structuring of reverse osmosis membranes for fouling resistance and improved flux performance, J. Mater, Chem., 2010, 20 (22), 4642-4652; Malaisamy et al., Development of reactive thin film polymer brush membranes to prevent biofouling, J. Membr. Sci., 2010, 350, 10; Varin et al., Biofouling and cleaning effectiveness of surface nanostructured reverse osmosis membranes, J. Membr. Sci., 2013, 446, 10; Varin et al., Wettability of terminally anchored polymer brush layers on a polyamide surface, J. Colloid Interface Sci., 2014, 436, 286-95; Cohen et al., Membrane Surface Nanostructuring with Terminally Anchored Polymer Chains, In Functional Nanostructured Materials and Membranes for Water Treatment, Duke et al. Ed.; Wiley-VCH Verlag: New York, 2013, p 40; Rahaman et al., Control of biofouling on reverse osmosis polyamide membranes modified with biocidal nanoparticles and antifouling polymer brushes, J. Mater. Chem., B 2014, 2, 8; Cohen et al., Fouling and scaling resistant nanostructured reverse osmosis membranes, U.S. Pat. No. 8,445,076). These hydrophilic fouling-resistant brushes are located above a selective membrane film, are usually nonselective, and only provide a barrier to foulants (e.g., proteins and natural organic matter), while our hydrophobic brushes are the selective layer attached to a nonselective support layer. This and excellent performance of our synthetic membranes are the novel aspects of our invention. In one case, a hydrophilic tethered brush had selective properties for salt rejection, but this is quite different from the selective hydrophobic brush presented here because it is not suitable for recovery of organics with pervaporation (Cohen et al., Fouling and scaling resistant nanostructured reverse osmosis membranes, U.S. Pat. No. 8,445,076).

Pervaporation is a combination of a membrane (rate governed) and thermal (equilibrium) process and is most widely used alone or in combination with distillation. The advantage of using this process is that it easily breaks azeotropes and fractionates closely boiling liquids, in contrast to thermal processes (Baker, Pervaporation. In Membrane Technology and Applications, 3rd ed., Baker, Ed.; John Wiley & Sons: New York, 2012, pp 379-416). An important example is the dehydration of ethanol and isopropanol water mixtures in the pharmaceutical and fine chemical industries. The first step is to distill water from ethanol until the azeotrope is formed (at ~10% water) and then, in the second step, use pervaporation to yield a final water content of <1%. This purity of ethanol allows it to be used as a fuel. An aqueous stream containing alcohol is passed across a pervaporation membrane allowing the alcohol to dissolve into the membrane and then diffuse down a chemical potential gradient to the second face of the membrane where the alcohol evaporates into a carrier gas or is allowed to re-condense at a cooled surface, while the retained polar component (water in this case) concentrates on the feed side. The difference in chemical potential between the two phases is the driving force for permeation. Passing water through the membrane in preference to alcohol necessitates a hydrophilic membrane while the reverse requires a hydrophobic membrane. Thus, material choice is critical for selectivity of pervaporation membranes, since the mechanism of transport is based on the solution-diffusion model (Lee et al., Sorption, Diffusion, and Pervaporation of Organics in Polymer Membranes, J. Membr. Sci., 1989, 44 (2), 161-181). Rubbery poly(dimethylsiloxane) (PDMS, also called silicone rubber or Sil5 and Sil20 here) is used commercially to selectively pass ethanol in preference to water, and relies on sorption selectivity rather than diffusion selectivity (Blume et al., The Separation of Dissolved Organics from Water by Pervaporation, J. Membr. Sci., 1990, 49 (3), 253-286), while the opposite holds for poly (vinyl alcohol), which is hydrophilic and is both sorption and diffusion selective for water passage (Chapman et al., Membranes for the Dehydration of Solvents by Pervaporation, J. Membr. Sci., 2008, 318 (1), 5-37). These materials plus cellulose acetate have been used in asymmetric or composite structures for the past 30 years. Clearly, new materials with superior performance are needed. We disclose a new class of superior performing hydrophobic brush membranes (i.e., our synthetic membranes) for the selective recovery of isobutanol for use as a biofuel that are simple to prepare, easy to scale-up, and environmentally friendly. Our synthetic membranes are also useful for selective recovery of other volatile organic compounds.

Moreover, the present invention also relates to reverse osmosis processes and purification of water methods. More than 1 billion people worldwide lack access to potable water, and almost 2 million children die each year for want of clean water and adequate sanitation. California is already struggling with drought and water scarcity is predicted to increase in the western states of the United States during the next 30 years. The increase in population, energy needs, and the industrial development of countries like China, India, and Brazil will lead to water supply challenges. Clearly, during the next 30 years, stresses to the available water supply will increase.

Three methods that can increase our water supply include desalination, purification of low-quality water (brackish groundwater and storm water), and purification and reuse of wastewater. Reverse osmosis has moved from cellulose acetate based membranes to hydrophilic polyamide based membranes. Current desalination membrane systems are more efficient than the thermal desalination systems of the past and have improved significantly since their inception approximately 60 years ago. Desalination of brackish and seawater is one of several nontraditional sources of water being considered to supplement current potable water needs and complement water-reuse strategies. Reclaiming, recycling, and reusing water creates new sources of high-quality water supply and addresses these challenges.

As has been reported, the economics of desalination has changed dramatically over the past three decades, with improvements in energy recovery and membrane technology. Desalting brackish groundwater is a growing practice in the United States, and with 96% of the world's water in the oceans, seawater desalination is clearly a major opportunity for future water needs. According to the International Desalination Association, in 2013 there were more than 17,000 desalting units globally, with installed capacity of 21.1 billion gallons per day (80 million $m^3$ $day^{-1}$). Japan is building a megaton plant (1 million $m^3$ $day^{-1}$) that is scheduled to open in 2020. Here, we disclose methods of use of our synthetic membranes for purification of water from ionic solutions of water and inorganic ions.

We also disclose methods of use of our synthetic membranes for isolating non-polar gases by gas fractionation. Gas separations operate according to the solution diffusion model or the Knudsen diffusion model. In the solution diffusion model (dense), the selectivity of the gas is dependent upon the diffusion selectivity and the sorption selectivity of the membranes. Smaller gas molecules will diffuse through the membrane faster than larger ones. Also, if the sorption of the gas is high, then the gas will permeate the membrane faster. Sorption is dependent upon the condensability of the molecules transporting through the membrane (called permeant) Larger molecules are usually more condensable and therefore will have a higher sorption into the membrane. In the Knudsen diffusion model (porous), convective flow, Knudsen diffusion, and molecular sieving will govern the selectivity. If the pores are too large (0.1-10 µm), then there will be no selectivity, as in convective flow. If the pores are less than 0.1 µm, they are on the same order as the mean free path of the gas. Then they will follow Knudsen diffusion and the transport rate will be inversely proportional to the square root of the molecular weight. Even smaller pores (5-20 Å) operate under the surface diffusion model and are more complex. More information about gas separation methods can found in Baker R W. 2004. Gas Separation, In Membrane Technology and Applications, pp. 301-53: John Wiley & Sons, Ltd, 2nd edition.

SUMMARY OF THE INVENTION

The present invention relates to methods of isolating volatile organic compounds from volatile organic mixtures comprising water and volatile organic compounds. Such methods are useful for selective recovery of biofuels and for other applications such as purification of chemical intermediates and other commodity chemicals.

The present invention also relates to methods of purifying water from ionic solutions comprising water and inorganic ions. Such methods are useful for desalination of brackish water or seawater and for other applications such as purifying wastewater and other recycled water feed streams.

The present invention also relates to methods of isolating non-polar gases by gas fractionation.

Thus, in one embodiment, the invention is directed to a method of isolating volatile organic compounds with a synthetic membrane, the synthetic membrane comprising a hydrophobic polymer layer located on a polymeric membrane support layer, wherein the hydrophobic polymer layer comprises a plurality of polymer units covalently bonded to the polymeric membrane support layer, wherein each polymer unit comprises a polymerized plurality of vinyl monomers, the method comprising:

contacting a volatile organic mixture with the hydrophobic polymer layer of the synthetic membrane, the volatile organic mixture comprising water and volatile organic compounds; and removing volatile organic compounds from the polymeric membrane support layer of the synthetic membrane by a process of pervaporation.

In another embodiment, the invention is directed to a method of purifying water with a synthetic membrane, the synthetic membrane comprising a hydrophobic polymer layer located on a polymeric membrane support layer, wherein the hydrophobic polymer layer comprises a plurality of polymer units covalently bonded to the polymeric membrane support layer, wherein each polymer unit comprises a polymerized plurality of vinyl monomers, the method comprising:

contacting an ionic solution with the hydrophobic polymer layer of the synthetic membrane, the ionic solution comprising water and inorganic ions; and removing water from the polymeric membrane support layer of the synthetic membrane by a process of reverse osmosis.

In another embodiment, the invention is directed to a method of isolating non-polar gas compounds with a synthetic membrane, the synthetic membrane comprising a hydrophobic polymer layer located on a polymeric membrane support layer, wherein the hydrophobic polymer layer comprises a plurality of polymer units covalently bonded to the polymeric membrane support layer, wherein each polymer unit comprises a polymerized plurality of vinyl monomers, the method comprising.

contacting a gas mixture with the hydrophobic polymer layer of the synthetic membrane, the gas mixture comprising polar gas compounds and non-polar gas compounds; and removing non-polar gas compounds from the polymeric membrane support layer of the synthetic membrane by a process of gas fractionation.

The methods and the synthetic membranes of the invention are advantageous because they are effective and can be prepared quickly and at a relatively low cost.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 3(B) shows separation factor versus isobutanol volume percent. As alcohol vol % increases, between 1 and 6% (v/v), $\alpha$ increases, below 1% (v/v), and decreases above 4% (v/v) due to swelling and solvent effects, respectively. The permeation flux exhibited inverse behavior. (C) Separation factor ($\alpha$) decreases linearly with increasing permeation flux (J) [C18 grafted membrane (●), Sil20 membrane (♦)] (y=ax+b where a=−16 and b=24; $R^2$=0.57; parallel lines represent one standard deviation of error from the fitted line).

DETAILED DESCRIPTION OF THE INVENTION

Figure 1:
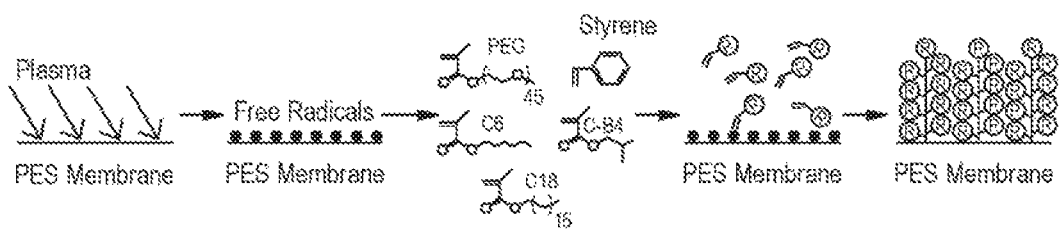
FIG. 1 shows schematics and process diagram for synthesizing and testing brush membranes with in vitro enzymatic reaction to produce isobutanol. (A) Atmospheric pressure plasma-induced graft polymerization (APP) of vinyl monomer on poly(ether sulfone) (PES) membranes. Monomers: polyethylene glycol (PEG), styrene, hexyl methacrylate (C6), isobutyl methacrylate (C-B4), and stearyl methacrylate (C18). Vinyl functional groups are labeled R. (B) Laboratory scale pervaporation apparatus showing the liquid recycle loop and the product vapor stream. (C) Two-step in vitro enzymatic reaction to produce isobutanol from ketoisovaleric acid, keto-acid decarboxylase (KdcA), alcohol dehydrogenase (ADH), and formate dehydrogenase (FDH).
Figure 1:
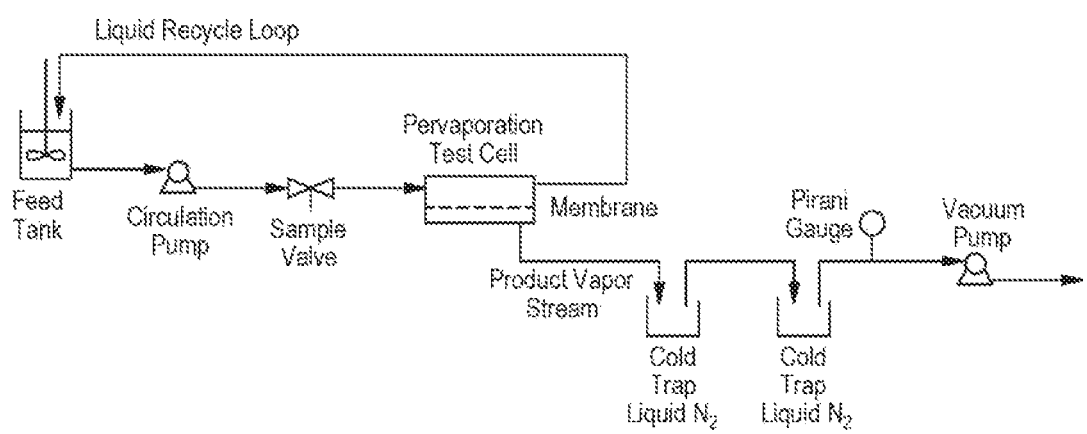
Figure 1:
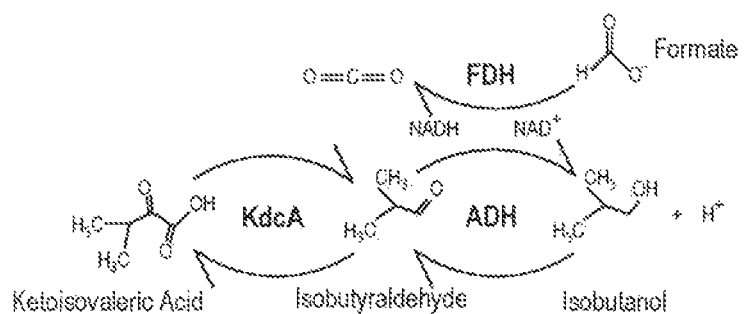

In the following specification and the claims which follow, reference will be made to a number of terms, which shall be defined to have the following meanings.

The singular forms "a", "an", and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

The term "alkyl" is intended to include linear, branched, or cyclic hydrocarbon structures and combinations thereof. A combination would be, for example, cyclopropylmethyl. As used herein, the term "alkyl" encompasses lower alkyls, which are alkyl groups of from 1 to 6 carbon atoms. Examples of lower alkyl groups include methyl, ethyl, propyl, isopropyl, butyl, s- and t-butyl and the like. As used herein, the term "alkyl" also encompasses alkyls having from 1 to 20 carbon atoms. Cycloalkyl is a subset of alkyl and includes cyclic hydrocarbon groups of from 3 to 8 carbon atoms. Examples of cycloalkyl groups include c-propyl, c-butyl, c-pentyl, norbornyl, and the like.

As used herein, the term "volatile organic compounds" refers to any organic compound having an initial boiling point less than or equal to 250° C. measured at a standard atmospheric pressure of 1 atm (101.3 kPa) Volatile organic compounds have high vapor pressure and are easily vaporized or evaporated. Volatile organic compounds exclude carbon monoxide, carbon dioxide, carbonic acid, metallic carbides or carbonates and ammonium carbonate, which participate in atmospheric photochemical reactions.

As used herein, the term "inorganic ions" refers to monovalent and divalent ions of inorganic compounds, such as ions of inorganic salts.

As used herein, the term "process of pervaporation" refers to a processing method for the separation of mixtures of liquids by partial vaporization through our synthetic membrane.

The term "removing", as used in "removing volatile organic compounds from the polymeric membrane support layer of the synthetic membrane by a process of pervaporation", refers to any fashion of removing, collecting, accumulating, or concentrating volatile organic compounds as they exit the polymeric membrane support layer of the synthetic membrane in a pervaporation process. The term "removing" in this context includes but is not limited to isolation of volatile organic compounds from impurities.

As used herein, the term "process of reverse osmosis" refers to a water purification technology that uses our synthetic membrane to remove water from an ionic solution. In reverse osmosis, an applied pressure is used to overcome osmotic pressure and impart desirable water transport.

The term "removing", as used in "removing water from the polymeric membrane support layer of the synthetic membrane by a process of reverse osmosis", refers to any fashion of removing, collecting, accumulating, or concentrating water molecules as they exit the polymeric membrane support layer of the synthetic membrane in a reverse osmosis process. The term "removing" in this context includes but is not limited to isolation of water from impurities.

As used herein, the term "seawater" refers to water from a sea or ocean. Ion concentration in seawater is usually from about 10,000 ppm to about 44,000 ppm. Common ions in seawater are chloride, sodium, sulfate, magnesium, calcium, potassium, bicarbonate, strontium, bromide, borate, fluoride, boron, silicate, and iodide.

As used herein, the term "brackish water" refers to water that has more salinity than fresh water, but not as much as seawater. It may result from mixing of seawater with fresh water, as in estuaries, or it may occur in brackish fossil aquifers.

The water that may be purified by the methods disclosed herein may also be water from rivers, lakes, and other surface waters. Ion concentration in brackish water is usually higher than in fresh water and less than about 10,000 ppm. Common ions in brackish water are chloride, sodium, sulfate, magnesium, calcium, potassium, bicarbonate, strontium, bromide, borate, fluoride, boron, silicate, and iodide.

As used herein, the term "isolating volatile organic compounds" refers to increasing concentration of volatile organic compounds. Isolated volatile organic compounds may include trace impurities, such as trace solvents.

As used herein, the term "purifying water" refers to increasing concentration of water. Purified water may include trace impurities, such as trace amounts of inorganic ion impurities.

As used herein, the term "polymeric membrane support layer" refers to any membrane made out of a polymer material and having pores. In one embodiment, the pores have a size of from about 1 nm to about 10 nm. The polymeric membrane support layer may be a light sensitive poly(ether sulfone) membrane support layer. The polymeric membrane support layer may also be made from such materials as polysulfone, cellulose, cellulose acetate, polyvinylidene fluoride, polyimide, polyethylene, polypropylene, polyacrylonitrile, and polyethylene terephthalate. The thickness of the polymeric membrane support layer may be from about 10 µm to about 500 µm.

As used herein the term "light sensitive poly(ether sulfone) membrane support layer" refers to a nanofiltration membrane with a thickness of from about 210 µm to about 250 µm. The light sensitive poly(ether sulfone) membrane support layer may be made entirely of poly(ether sulfone).

Alternatively, the light sensitive poly(ether sultone) membrane support layer may have two layers. (1) a skin layer composed of poly(ether sulfone); and (2) a skin support layer. The skin support layer has a thickness of from about 50 nm to about 300 nm. In one embodiment, the poly(ether sulfone) skin layer has an average pore size of about 1 nm and a divalent salt rejection of 80-95% for $Na_2SO_4$. The skin support layer may be made from polysulfone, cellulose, cellulose acetate, polyvinylidene fluoride, polyimide, polyethylene, polypropylene, polyacrylonitrile, or polyethylene terephthalate. The skin support layer is porous.

As used herein, the term "vinyl monomers" refers to a compounds having a vinyl functional group, which are compounds of formula $R-CH=CH_2$, wherein R is any other group or atoms.

As used herein, the term "polymerized plurality of vinyl monomers" refers to two to more vinyl monomers covalently bound to each other through a process of polymerization.

The term "contacting", as used in "contacting a volatile organic mixture with the hydrophobic polymer layer of the synthetic membrane", refers to any method by which the volatile organic mixture comes into direct contact with and next to the hydrophobic polymer layer of the synthetic membrane.

The term "contacting", as used in "contacting an ionic solution with the hydrophobic polymer layer of the synthetic membrane", refers to any method by which the ionic solution comes into direct contact with and next to the hydrophobic polymer layer of the synthetic membrane.

The term "polar gas compounds", as used herein, refers to gas compounds with an uneven electron distribution resulting in a non-zero net dipole moment. Examples of polar gas compounds include carbon monoxide, ammonia, and hydrogen sulfide.

The term "non-polar gas compounds", as used herein, refers to gas compounds with an even electron distribution resulting in a net dipole moment of zero. Examples of non-polar gas compounds include carbon dioxide, hydrogen, helium, nitrogen, oxygen, carbon dioxide, methane, ethylene, low molecular weight alkanes (up to and including dodecane), and the noble gases.

The term "gas fractionation" refers to separation of one gas species from a mixture of gases. An example of gas fractionation process can be found in Baker R W. 2004, Gas Separation, In Membrane Technology and Applications, pp. 301-53: John Wiley & Sons, Ltd, 2nd edition.

The term "contacting", as used in "contacting a gas mixture with the hydrophobic polymer layer of the synthetic membrane", refers to any method by which the gas mixture comes into direct contact with and next to the hydrophobic polymer layer of the synthetic membrane.

The term "isolating non-polar gas compounds" refers to increasing concentration of non-polar gas compounds. Isolated non-polar gas compounds may include trace impurities.

In one embodiment, the invention is directed to a method of isolating volatile organic compounds with a synthetic membrane, the synthetic membrane comprising a hydrophobic polymer layer located on a polymeric membrane support layer, wherein the hydrophobic polymer layer comprises a plurality of polymer units covalently bonded to the polymeric membrane support layer, wherein each polymer unit comprises a polymerized plurality of vinyl monomers, the method comprising:

contacting a volatile organic mixture with the hydrophobic polymer layer of the synthetic membrane, the volatile organic mixture comprising water and volatile organic compounds; and removing volatile organic compounds from the polymeric membrane support layer of the synthetic membrane by a process of pervaporation.

In some embodiments, the hydrophobic polymer layer, in addition to the discussed above plurality of polymer units that are covalently bonded to the polymeric membrane support layer, further comprises a plurality of polymer units adhered via non-covalent bonds (for example, ionic bonds, hydrogen bonds, and/or Van der Waals forces) to the polymeric membrane support layer and/or to the plurality of polymer units that are covalently bonded to the polymeric membrane support layer. In such non-covalently bonded plurality of polymer units, each polymer unit comprises a polymerized plurality of vinyl monomers.

The polymeric membrane support layer may be a light sensitive poly(ether sulfone) membrane support layer.

Figure 1D:
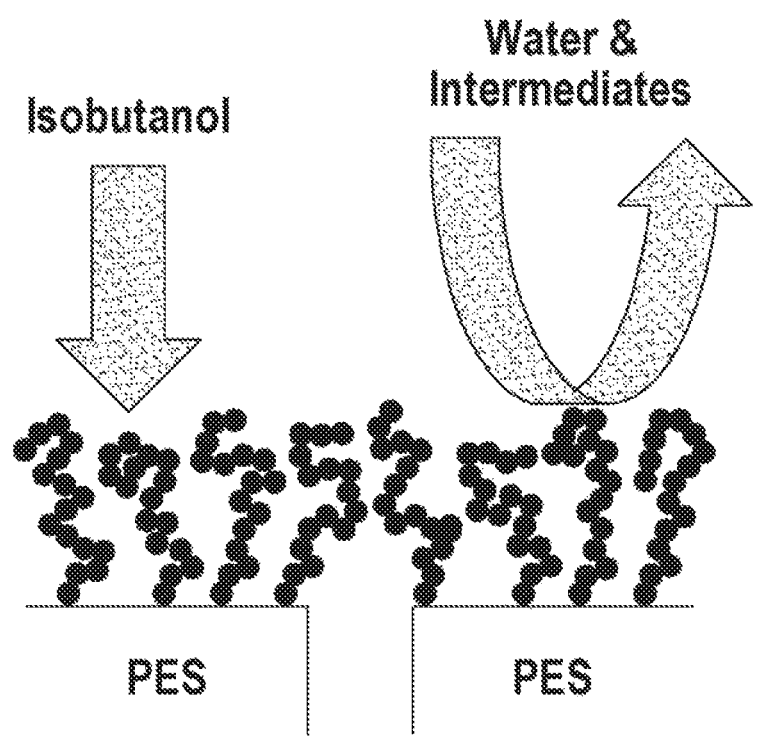
FIG. 1D shows a schematic representation of use of our synthetic membrane to isolate isobutanol.

The volatile organic compounds may be alcohols, such as, for example, isobutanol, ethanol, and longer chain alcohols. FIG. 1D shows a schematic representation of use of our synthetic membrane to isolate isobutanol.

In another embodiment, the volatile organic compounds are selected from the group consisting of isobutanol, isobutyraldehyde, ketoisovaleric acid, reduced nicotinamide adenine dinucleotide (NADH), formate, and mixtures thereof.

In another embodiment, the volatile organic compounds may be selected from alkanes, alkenes, alkynes, cycloalkanes, aromatics, alkyl halides, thiols, amines, ethers, thioethers, phenols, ketones, aldehydes, imines, carboxylic acids, esters, thioesters, amides, acyl phosphates, acid chlorides, phosphate monoesters, phosphate diesters, and mixtures thereof.

The present invention is also directed to a method of purifying water with a synthetic membrane, the synthetic membrane comprising a hydrophobic polymer layer located on a polymeric membrane support layer, wherein the hydrophobic polymer layer comprises a plurality of polymer units covalently bonded to the polymeric membrane support layer, wherein each polymer unit comprises a polymerized plurality of vinyl monomers, the method comprising:
- contacting an ionic solution with the hydrophobic polymer layer of the synthetic membrane, the ionic solution comprising water and inorganic ions; and
- removing water from the polymeric membrane support layer of the synthetic membrane by a process of reverse osmosis.

In some embodiments, the hydrophobic polymer layer, in addition to the discussed above plurality of polymer units that are covalently bonded to the polymeric membrane support layer, further comprises a plurality of polymer units adhered via non-covalent bonds (for example, ionic bonds, hydrogen bonds, and/or Van der Waals forces) to the polymeric membrane support layer and/or to the plurality of polymer units that are covalently bonded to the polymeric membrane support layer. In such non-covalently bonded plurality of polymer units, each polymer unit comprises a polymerized plurality of vinyl monomers.

The polymeric membrane support layer may be a light sensitive poly(ether sulfone) membrane support layer.

In one embodiment of the above method of purifying water, the ionic solution is a seawater. In another embodiment, the ionic solution is a brackish water.

The inorganic ions may be selected from the group consisting of chloride, sodium, sulfate, magnesium, calcium, potassium, bicarbonate, strontium, bromide, borate, fluoride, boron, silicate, iodide, and mixtures thereof.

In the above methods, the polymeric membrane support layer may have a pore size of from about 1 nm to about 10 nm. In one embodiment, the pore size is about 1 nm.

In the above methods, the vinyl monomers are monomers having a vinyl functional group, which are compounds of formula R—CH=CH$_2$, wherein R is any other group or atoms.

In one embodiment, the vinyl monomers are $C_{1-20}$ alkyl methacrylate monomers, such as $C_1$ alkyl methacrylate, $C_2$ alkyl methacrylate, $C_3$ alkyl methacrylate, $C_4$ alkyl methacrylate, $C_5$ alkyl methacrylate, $C_6$ alkyl methacrylate, $C_7$ alkyl methacrylate, $C_8$ alkyl methacrylate, $C_9$ alkyl methacrylate, $C_{10}$ alkyl methacrylate, $C_{11}$ alkyl methacrylate, $C_{12}$ alkyl methacrylate, $C_{13}$ alkyl methacrylate, $C_{14}$ alkyl methacrylate, $C_{15}$ alkyl methacrylate, $C_{16}$ alkyl methacrylate, $C_{17}$ alkyl methacrylate, $C_{18}$ alkyl methacrylate, $C_{19}$ alkyl methacrylate, and $C_{20}$ alkyl methacrylate. Some examples of $C_{1-20}$ alkyl methacrylate monomers are methyl methacrylate (C1), ethyl methacrylate (C2), butyl methacrylate (C4), hexyl methacrylate (C6), decyl methacrylate (C10), tridecyl methacrylate (C13), and stearyl methacrylate (C18).

In another embodiment, the vinyl monomers are polyethylene glycol monomers. In yet another embodiment, the vinyl monomers are styrene monomers.

In one embodiment, the method is a method of isolating volatile organic compounds with a synthetic membrane and the vinyl monomers are $C_{18}$ alkyl methacrylate monomers, such as stearyl methacrylate monomers.

In another embodiment, the method is a method of purifying water with a synthetic membrane and the vinyl monomers are C<alkyl methacrylate monomers, such as hexyl methacrylate monomers.

When the polymeric membrane support layer is a light sensitive poly(ether sulfone) membrane support layer, the synthetic membrane of the above described methods may be prepared by a method which includes:
- irradiating a surface of the light-sensitive poly(ether sulfone) membrane support layer; and
- contacting a monomer solution with the surface of the light-sensitive poly(ether sulfone) membrane support layer, the monomer solution comprising vinyl monomers and a solvent.

When the light-sensitive poly(ether sulfone) membrane support layer has a skin layer composed of poly(ether sulfone) and a skin support layer, the surface of the light-sensitive poly(ether sulfone) membrane support layer is on the side of the light-sensitive poly(ether sulfone) membrane support layer that has a skin layer composed of poly(ether sulfone).

In one embodiment, irradiating the surface of the light-sensitive poly(ether sulfone) membrane support layer comprises exposing the surface of the light-sensitive poly(ether sulfone) membrane support layer to atmospheric pressure plasma for a time period of from about 2 minutes to about 10 minutes. Plasma head to membrane distance may be 5-25 mm, power may be in the range of 120-160 W, He Flow Rate may be 30 L min$^{-1}$, O$_2$ Flow Rate may be 0.2-0.6 L min$^{-1}$, and Plasma head speed may be 1-30 mm s$^{-1}$.

In another embodiment, irradiating the surface of the light-sensitive poly(ether sulfone) membrane support layer comprises exposing the surface of the light-sensitive poly(ether sulfone) membrane support layer to ultraviolet light for a time period of from about 10 seconds to about 5 minutes.

In one embodiment, contacting the monomer solution with the surface of the light-sensitive poly(ether sulfone) membrane support layer is performed at a temperature of from about 60° C. to about 70° C. In another embodiment, the vinyl monomers are polyethylene glycol monomers, and contacting the monomer solution with the surface of the light-sensitive poly(ether sulfone) membrane support layer is performed at a temperature of from about 60° C. to about 100° C.

In one embodiment, contacting the monomer solution with the surface of the light-sensitive poly(ether sulfone) membrane support layer is performed for a time period of from about 10 minutes to about 24 hours.

When the polymeric membrane support layer is not a light sensitive poly(ether sulfone) membrane support layer, the synthetic membrane of the above described methods may be prepared by a method which includes:
- contacting an initiator with a surface of the polymeric membrane support layer; irradiating the surface of the polymeric membrane support layer; and
- contacting a monomer solution with the surface of the polymeric membrane support layer, the monomer solution comprising vinyl monomers and a solvent.

Polymeric membranes that are made from materials that are other than a light sensitive poly(ether sulfone) membrane support layer include polysulfone, cellulose, cellulose acetate, polyvinylidene fluoride, polyimide, polyethylene, polypropylene, polyacrylonitrile, and polyethylene terephthalate.

The initiator induces radical formation on the surface of the polymeric membrane support layer when exposed to an irradiation source. The initiators are known in the art. One example on an initiator is benzophenone. Other examples of initiators are di-tert-butyl peroxide, dibenzoyl peroxide, methyl ethyl ketone peroxide, acetone peroxide peroxydisulfate salts, azobisisobutyronitrile, and 1,1'-Azobis(cyclohexanecarbonitrile) (ABCN).

For all of the above methods for preparation of the synthetic membrane, the molar concentration of the vinyl monomers in the monomer solution may be from about 0.01 M to about 9.0 M.

In one embodiment, the method is a method of isolating volatile organic compounds with a synthetic membrane, the vinyl monomers are C18 alkyl methacrylate monomers, and the molar concentration of the $C_{18}$ alkyl methacrylate monomers in the monomer solution is about 1.0 M.

In another embodiment, the method is a method of purifying water with a synthetic membrane, the vinyl monomers are $C_6$ alkyl methacrylate monomers, and the molar concentration of the $C_6$ alkyl methacrylate monomers in the monomer solution is about 4.0 M.

The invention is also directed to a method of isolating non-polar gas compounds with a synthetic membrane, the synthetic membrane comprising a hydrophobic polymer layer located on a polymeric membrane support layer, wherein the hydrophobic polymer layer comprises a plurality of polymer units covalently bonded to the polymeric membrane support layer, wherein each polymer unit comprises a polymerized plurality of vinyl monomers, the method comprising:
    contacting a gas mixture with the hydrophobic polymer layer of the synthetic membrane, the gas mixture comprising polar gas compounds and non-polar gas compounds; and
    removing non-polar gas compounds from the polymeric membrane support layer of the synthetic membrane by a process of gas fractionation.

In some embodiments, the hydrophobic polymer layer, in addition to the discussed above plurality of polymer units that are covalently bonded to the polymeric membrane support layer, further comprises a plurality of polymer units adhered via non-covalent bonds (for example, ionic bonds, hydrogen bonds, and/or Van der Waals forces) to the polymeric membrane support layer and/or to the plurality of polymer units that are covalently bonded to the polymeric membrane support layer. In such non-covalently bonded plurality of polymer units, each polymer unit comprises a polymerized plurality of vinyl monomers.

The non-polar gas compounds are selected from the group consisting of hydrogen, helium, nitrogen, oxygen, carbon dioxide, ethylene, one or more $C_{1-12}$ alkanes, one or more noble gases, and mixtures thereof. $C_{1-12}$ alkanes include methane, ethane, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, and $C_{12}$ alkyl. Noble gases include helium (He), neon (Ne), argon (Ar), krypton (Kr), xenon (Xe), and radon (Rn).

The polar gas compounds may be selected from the group consisting of carbon monoxide, oxygen, hydrogen sulfide, and mixtures thereof.

The above described synthetic membranes may be used in our methods of isolating non-polar gas compounds. These synthetic membranes may be prepared by any of the above described methods.

This written description uses examples to disclose embodiments of the invention, including the best mode, and also to enable any person skilled in the art to practice the invention, including making and using any devices or systems and performing any incorporated methods. The patentable scope of the invention is not limited to the scope of the provided examples, and may include other examples that occur to those skilled in the art. Such other examples are intended to be within the scope of the claims if they have structural elements or method steps that do not differ from the literal language of the claims, or if they include equivalent structural elements or method steps with insubstantial differences from the literal language of the claims.

EXAMPLES

Pervaporation (PV) Examples

Example 1

Materials and Methods

All materials and reagents were used as received. Isobutanol, isobutyraldehyde, ketoisovaleric acid, β-nicotinamide adenine dinucleotide [reduced] (NADH), formate, poly(ethylene glycol) methyl ether methacrylate (n=45) (hydrophilic control), styrene, hexyl methacrylate, isobutyl methacrylate, and stearyl methacrylate monomers were purchased from Sigma-Aldrich Chemicals (Milwaukee, Wis.). Rubbery poly(dimethylsiloxane) (PDMS, also called silicone rubber or Sil5 and Sil20 here) membranes were provided by Membrane Technology and Research (MTR). NADIR-NP030 poly(ether sulfone) (PES) nanofiltration membranes (~1 nm pore size) were provided by MCRODYN-NADIR. For preparation of thin PES films via spin coating, solutions were prepared using a 1% (w/v) PES solution in dichloromethane (DCM) deposited onto $SiO_2$ wafers.

Example 2

Pervaporation—Atmospheric Pressure Plasma Polymerization (APP)

PES membrane sheets were cut to 6.75 cm×6.75 cm and were presoaked in deionized (DI) water overnight prior to modification. The membranes were then exposed to an atmospheric pressure plasma (APP) source (Model ATOMFLO, Surfx Technologies LLC, Culver City, Calif.) at a helium flow rate of 30.0 L min$^{-1}$, an oxygen flow rate of 0.4 L min-, and a source-to-membrane distance of 20 mm. The plasma source was operated at 140 V and driven by a radio frequency power at 27.12 MHz. An XYZ Robot (Surfx Technologies LLC, Culver City, Calif.) was used to control the plasma source over the plate with a scan speed of 6 mm s$^{-1}$. After exposure to the plasma and subsequent formation of radicals at the membrane surface, the membranes were soaked in 40 mL of various different monomer solutions. Graft polymerization was immediately initiated at 60 t 1° C. for 2 h. The reaction was terminated by adding pre-filtered DI water (filtered using a 0.22 μm PES Stericup. Millipore. Billerica, Mass.). The membrane sheets were then soaked and rinsed with DI water for 24 h to remove any homopolymer or unreacted monomer residue from the membrane surfaces.

Example 3

Attenuated Total Reflectance-Fourier Transform Infrared Spectroscopy (ATR-FTIR)

PES membrane strips were cut to 1.0 cm 7.0 cm and were presoaked in DI water overnight prior to modification. The membranes were then exposed to an atmospheric pressure plasma (APP) source using the same conditions as those applied to the membrane sheets. After exposure to the plasma and subsequent formation of radicals at the membrane surface, the membranes were soaked in 8 mL of various different monomer solutions. Graft polymerization was immediately initiated again, following the same procedure as applied to the membrane sheets. ATR-FTIR spectra (Magna-IR 550 Series II, Nicolet Instruments, Madison, Wi) were collected for all monomer concentrations used in order to calculate DG. All spectra were collected using 256 scans at a resolution of 4 cm$^{-1}$ over the range 4000-700 cm$^{-1}$ with an incident angle of 450. Penetration of the IR beam was 0.1-1.0 mm. The system was cooled with liquid nitrogen, and a new background was collected before each sample. DG is defined as the ratio of the carbonyl peak at ~1715 cm$^{-1}$ to an internal reference peak of the poly(ether sulfone) membrane at 1578 cm$^{-1}$. All data were collected, and peak absorbances were measured using Omnic 7.0.

Example 4

Pervaporation

Membrane sheets were tested in a stainless steel patch clamp membrane module A rubber gasket was used to prevent leaks and maintain a constant vacuum pressure. The liquid recycle loop flowed the feed at 80±0.5 mL min$^{-1}$. The pressure on the permeate side of the membrane was held constant at 1±0.2 mbar by a turbomolecular drag pumping station vapor deposition vacuum pump (TSH 071 E, Pfeiffer Vacuum Technology AG, Germany). The system was run until ~4 mL of liquid permeated through the membrane. Samples from the recycle loop were taken every 30 min, and a final permeate sample was taken from the cold traps for analysis by GC. PV feed conditions: isobutanol 6, 5, 4, 1, 0.5, and 0% (v/v); ketoisovaleric acid 4 mM; isobutyraldehyde 2% (v/v); formate 1 M; NADH 0.6 mM.

Example 5

Gas Chromatography

GC: spectra were recorded (Agilent 6890N, Agilent Technologies, Santa Clara, Calif.). The following parameters were used to perform the analysis: carrier gas helium; inlet temperature 150° C.; 50:1 split ratio; constant column flow 3.3 mL min$^{-1}$; oven temperature 35° C.; flame ionization detector temperature 275° C.; make-up gas helium at 45 mL min$^{-1}$. Each sample (1 µL) was injected into the system, and the spectra were recorded over 3 min.

Example 6

Spin-Coating

PES was spin-coated onto SiO$_2$ wafers using an 8 in. Headway Spinner (Headway Research, Inc., Garland, Tex.) Thin PES films were prepared using a 1% (w/v) PES solution in dichloromethane (DCM). The spin-coating program consisted of three steps: the solution was deposited onto the SiO$_2$ surface and spun with a ramp speed of 1000 rpm s$^{-1}$ until it reached 3000 rpm, then it spins at 3000 rpm for 30 s, then it ramps down to zero at 1000 rpm s$^{-1}$, and then it stops. The deposited films were then kept covered at room temperature until they were measured with atomic force microscopy (AFM). These films were prepared in order to measure the thickness of the grafted layer. The hard SiO$_2$ substrate gave much better AFM results than the soft PES membrane strips.

Example 7

AFM Measurements

Atomic force microscopy (AFM; MFP 3D, Asylum Research, Santa Barbara, Calif.) images of spin-coated PES on SiO$_2$ wafers were obtained. This was used to measure the thickness of the grafted layer in either water or isobutanol. A scratch was made using a razor blade through the middle of the sample down to the SiO$_2$ substrate. The height of the layer was then measured from the substrate to the top of the film. The film was then modified by grafting 5 mL of 1 M C18 to the surface using UV-induced radical polymerization (as described previously in Zhou et al., High Throughput Synthesis and Screening of New Protein Resistant Surfaces for Membrane Filtration, AIChE J. 2010, 56 (7), 1932-1945, and in Zhou et al., High Throughput Discovery of New Fouling-Resistant Surfaces, J. Mater. Chem., 2011, 21 (3), 693-704) and then the height was measured again. An average of different height measurements was used to calculate the average thickness of the grafted layer. The height difference was measured using IGOR 6. Images were collected in the presence of either water or isobutanol using either tapping (before grafting) or contact modes (after grafting) using a v-shaped tip.

Example 8

Formation of Grafted Brush Membranes

In order to selectively pass isobutanol through a membrane from an aqueous solution of 0.5-6.0% (v/v), we graft-polymerized hydrophobic aliphatic monomers onto a light-sensitive PES nanofiltration membrane. Atmospheric pressure plasma induced graft polymerization (APP) was used together with our high throughput platform (FIG. 1A). (Gu et al., High Throughput Atmospheric Pressure Plasma-Induced Graft Polymerization for Identifying Protein-Resistant Surfaces, Biomaterials, 2012, 33 (5), 1261-1270). This approach created a library of PES nanofiltration membranes with different chemical and morphological surfaces, and allowed us to compare their pervaporation performance with that of commercial PDMS membranes. The graft density of the polymerized surface layer was measured and was determinant for the separation of isobutanol from an aqueous solution.

To test the new membrane brush structures (alone and as mixtures of grafted monomers of different lengths), their PV performance in recovering isobutanol from water was first measured and compared with the performance of PDMS membranes. The following monomers were grafted: isobutyl methacrylate (C-B4), hexyl methacrylate (C6), stearyl methacrylate (C18), and poly(ethylene glycol) methyl ether methacrylate (PEG) (n=45). Next, these same membranes were characterized by their degree of grafting (DG) followed by an assessment of their permeation flux and selectivity. This was performed by measuring not only isobutanol recovery, but also the selective transport of the other reactants and products present in an in vitro enzymatic reaction for the production of isobutanol from butyric acid. (Grimaldi et al., Toward Cell-Free Biofuel Production: Stable Immobilization of Oligomeric Enzymes, Biotechnol. Prog., 2014, 30 (2), 324-331).

Example 9

Characterization of Brush Membranes

Figure 2:
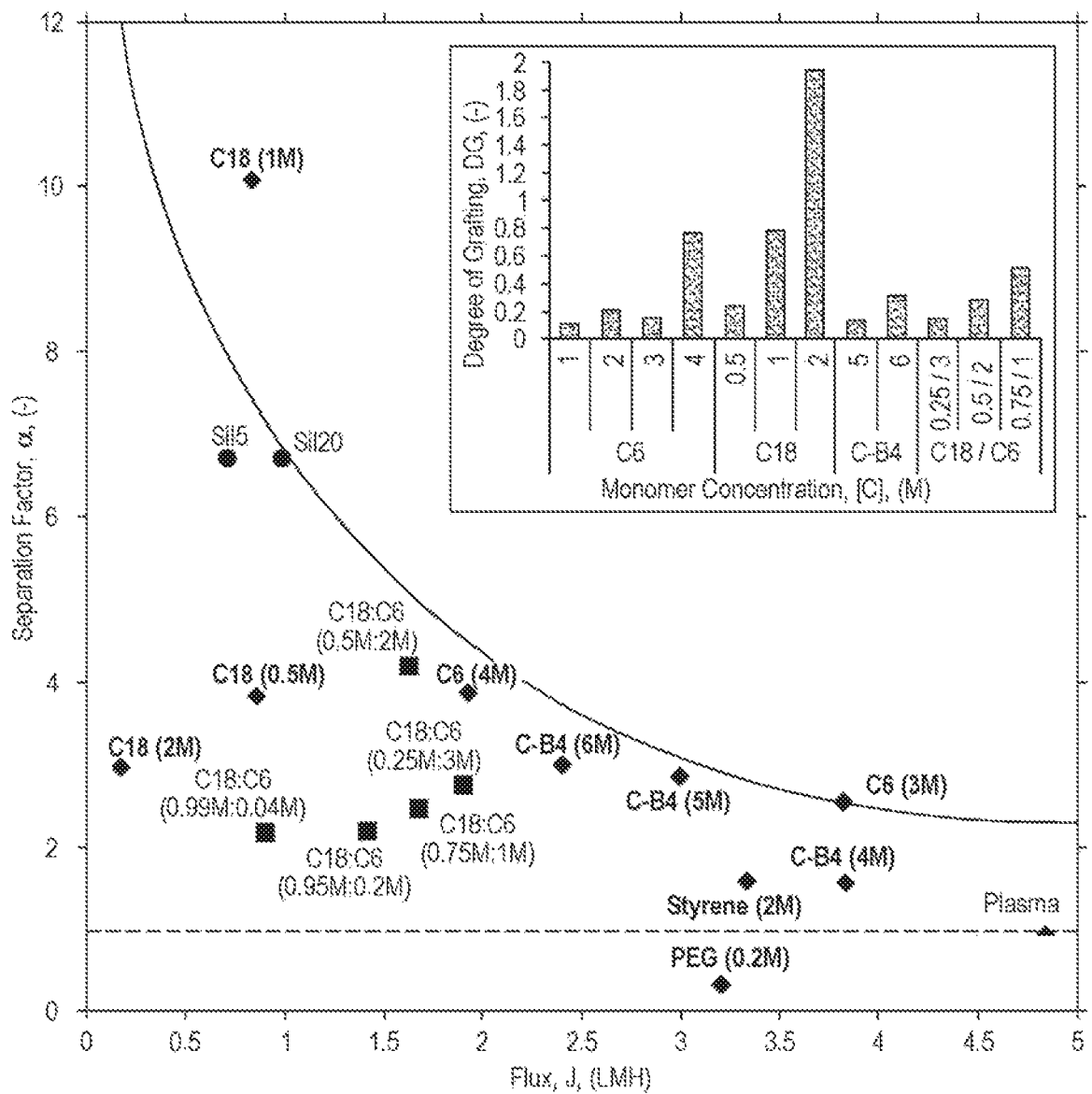
FIG. 2 shows a graph of separation factor ($\alpha$) versus permeation flux (J) for a range of different brush membranes tested with feed containing in vitro enzymatic reaction products. Commercial PDMS membranes (●) (Sil5 and Sil20), pure monomers (♦), C18:C6 monomer mixtures (■), and plasma only (◇); the dotted line indicates no separation ($\alpha$=1), and the solid line shows the lower limit of $\alpha$ versus J for performance of new membranes over existing membranes. Monomers: polyethylene glycol (PEG), styrene, hexyl methacrylate (C6), isobutyl methacrylate (C-B4), and stearyl methacrylate (C18). Insert: degree of grafting (DG) for vinyl monomers: hexyl methacrylate (C6), isobutyl methacrylate (C-B4), stearyl methacrylate (C18), and mixtures of C18/C6.

The degree of grafting (DG) was measured using attenuated total reflectance-Fourier transform infrared spectroscopy (ATR-FTIR) (FIG. 2, insert). DG was calculated by dividing the absorbance peak of the carbonyl (ester) in the monomer (~1720 cm$^{-1}$) by that of an internal benzene carbon-carbon double bond reference peak in the membrane polymer (1578 cm$^{-1}$) that was unaffected by the grafting process. The highest DG observed was for 2 M C18 with a value of 1.94. C18 also exhibited very high saturated hydrocarbon stretching at ~2950 cm$^{-1}$, as expected. In comparison, 1 M C18 showed a similar DG as 4 M hexyl methacrylate (C6) Experience suggests that DG values close to 2 are indicative of very high grafting density and not sparse monolayer surface coverage. Although isobutyl methacrylate (C-B4) has a similar structure to that of isobutanol, a concentration of 5 M was required to yield a sufficient grafting density (DG=0.13). Also, it did not perform well during pervaporation. This is likely due to its branched structure, preventing it from forming a dense brush layer.

In order to measure the thickness of the brush layer, a layer of PES was spin-coated onto the surface of an SiO2 substrate and then modified with C18 using the UV method as described previously (Zhou et al., High Throughput Synthesis and Screening of New Protein Resistant Surfaces for Membrane Filtration, AIChE J., 2010, 56 (7), 1932-1945; Zhou et al., High Throughput Discovery of New Fouling-Resistant Surfaces, J. Mater. Chem., 2011, 21 (3), 693-704). The thickness of the PES layer (before grafting) was 159-31 nm in water and 45±17 nm in isobutanol. The thickness after grafting was 208±44 nm in water, but could not be measured accurately in isobutanol. The isobutanol interacted strongly with the surface, forming a gel-like layer; therefore, the AFM tip was unable to accurately probe the surface. This observation qualitatively supports our findings from pervaporation, in that isobutanol is highly favored over water when interacting with our new C18 surface. Therefore, the approximate height of the modified layer is ~50 nm as measured by the height difference of the two layers. Note that the molecular structure resembles a tree with C18 branches emanating from the trunk. Molecular modeling suggests that a single fully stretched C18 branch extends about 2 nm (Eugene Wu, RPI, private communication).

Example 10

Pervaporation Performance of Grafted Brush Membranes

A custom pervaporation system (FIG. 1B) was used to quantify the flux of species that passed through each membrane. Gas chromatography (GC) analyses of the retentate and permeate were used to determine the molar separation factor $$\alpha = \frac{\left[\frac{x_{iso}}{x_w} \text{permeate}\right]}{\left[\frac{x_{iso}}{x_w} \text{retentate}\right]} \quad (1)$$

where $x_{iso}$ and $x_w$ are mole fractions for isobutanol and water, respectively.

In FIG. 2, the isobutanol selectivity (6% (v/v) isobutanol) over water is plotted against permeation flux of isobutanol for 10 single-grafted monomers. 5 different grafted mixtures of C18 with C6 monomers, and 2 commercial membranes (Sil5 and Sil20). Commercial PDMS membranes, Sil5 and Sil20, have an active layer thickness of 5 and 20 μm, respectively, and serve as the industry standard for hydrophobic PV membranes. Overall, the straight chain monomers exhibited much better pervaporation performance than the aromatic or branched monomers. This could be due to a higher, more ordered packing density caused by strong hydrophobic interactions between polymer chains, which led to a highly selective hydrophobic active layer. Unfortunately, mixing a long chain monomer, C18, and a short chain monomer, C6, did not result in increased flux (J) with equivalent or slightly lower selectivity (α). Instead, the selectivity dropped from 10.1 to 2-4. The shorter C6 monomer may have disrupted the densely packed grafted layer of pure grafted C18, decreasing α. The 1 M C18 brush membrane had a flux of J=0.8±0.2 LMH (L m$^2$ h$^{-1}$); this is comparable to the fluxes for Sil5 and Sil20 of J=0.7±0.1 LMH and 1±0.1 LMH, respectively. However, the separation factor for the C18 brush membrane was α=10.1±0.9 compared with α=6.7±0.1 and 6.7±0.1 for Sil5 and Sil20, respectively, which is a 1.5-fold increase. All the other single-grafted brush membranes had much higher fluxes (J>1.5 LMH) but with significantly lower selectivities (α<4). Addition of C6 to C18 in any amount reduced α significantly. C6 alone (at 3 M monomer concentration) exhibited the highest flux with J=3.8 LMH and α=2.5. Further work is underway to determine if one can move the C18 α-values to the right for higher fluxes.

Figure 3:
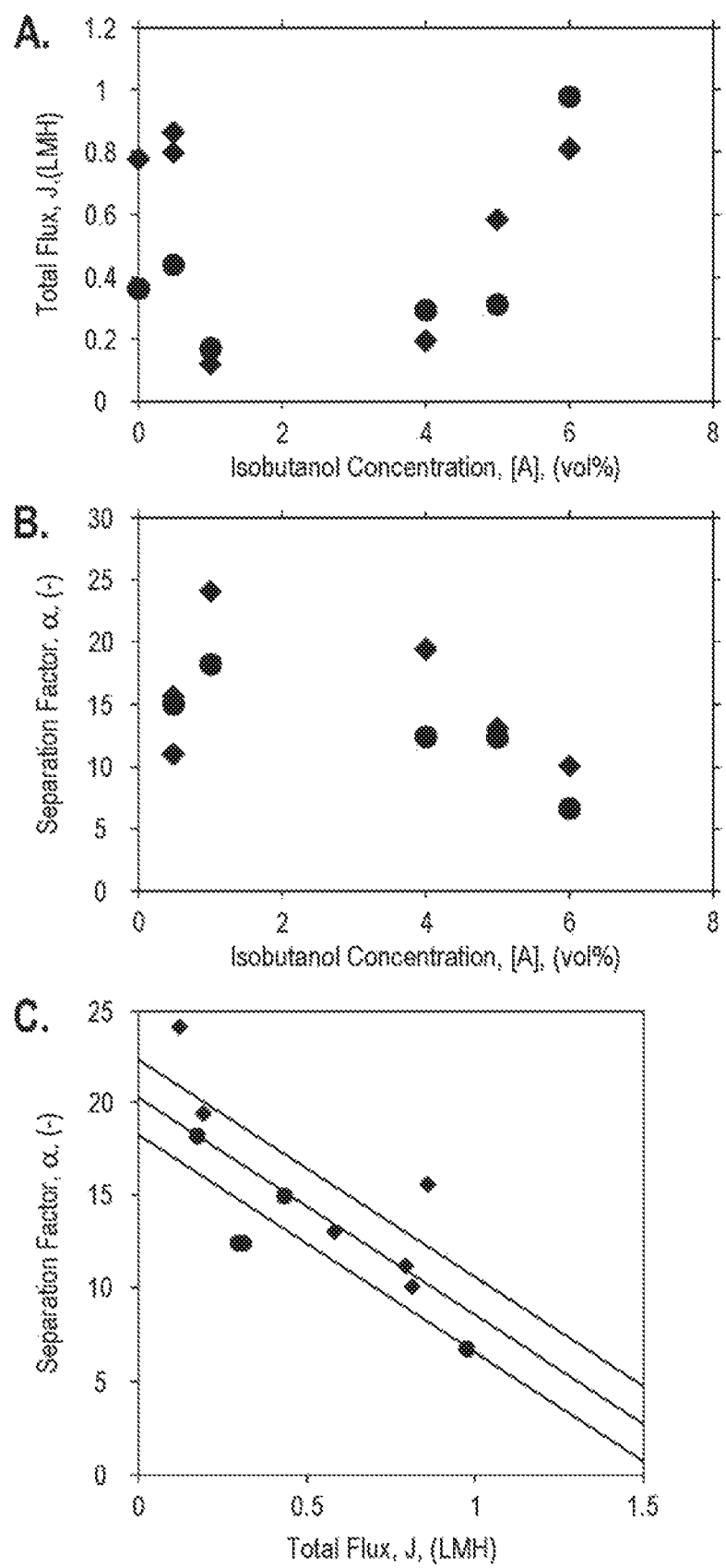
FIG. 3 shows our results in graphs (A), (B), and (C). (A) shows total permeation flux versus isobutanol volume percent in the feed. As alcohol vol % decreases, between 1 and 6% (v/v), the flux declines; below 1% (v/v) the flux increases again due to solvent effects on the membrane [C18 grafted membrane (●), Sil20 membrane (♦)].
Figure 4:
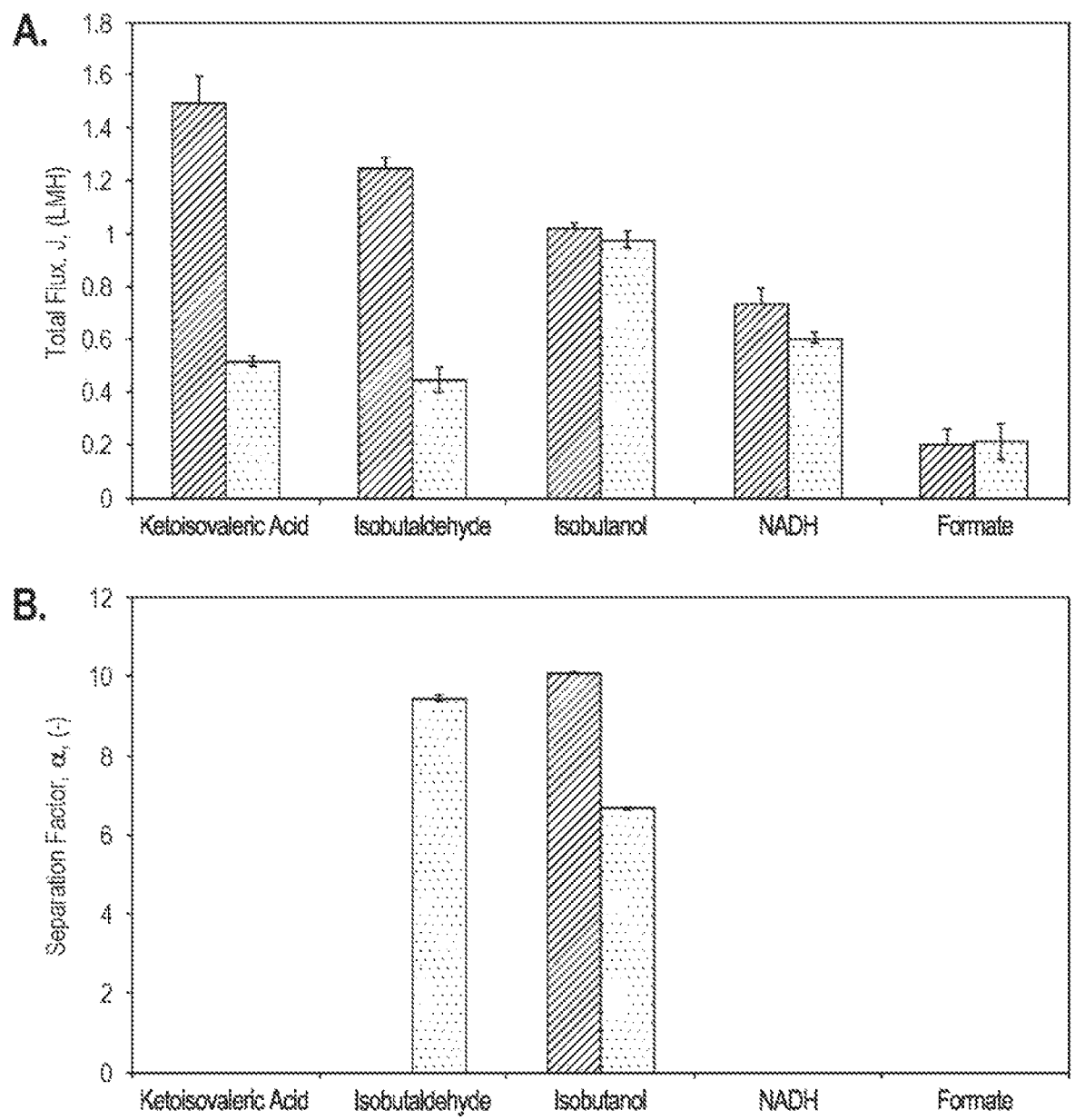
FIG. 4 shows our results in graphs (A) and (B). (A) Total permeation flux (J). (B) Separation factor ($\alpha$) for reaction components in water. Both the commercial PDMS (shaded pattern) and the new C18 grafted membranes (solid pattern) retained formate, f-nicotinamide adenine dinucleotide [reduced] (NADH), and ketoisovaleric acid. However, only the grafted membrane retained isobutyraldehyde. If a bar is present in (B), then that species permeated through the membrane.

Selectivity depends on diffusion rates and sorption amounts [$\alpha_{mem}$ m=$(D_i/D_j)(K_i/K_j)$, where D is the diffusion coefficient, K is the sorption coefficient, i is for isobutanol, and j is for water]. Often membranes used in pervaporation exhibit sorption-selectivity-control or diffusion-selectivity-control (Baker, R. W. Pervaporation. In Membrane Technology and Applications, 3rd ed., Baker, R. W., Ed.; John Wiley & Sons: New York, 2012; pp 379-416). Hydrophilic, rigid, cross-linked, glassy polymer systems, such as poly (vinyl alcohol), favor the sorption and permeation of water over more hydrophobic compounds ($K_j$>$K_i$). Additionally, diffusion selectivity favors smaller molecules (water) over larger ones (isobutanol) ($D_j$>$D_i$). Hydrophobic rubbery membranes, such as PDMS and our brush membranes, preferentially absorb the more hydrophobic organic compound (isobutanol). For rubbery materials, the diffusion selectivity term ($D_i/D_j$) is small (Baker, R. W. Pervaporation. In Membrane Technology and Applications, 3rd ed.; Baker, R. W., Ed.; John Wiley & Sons: New York, 2012, pp 379-416). Therefore, our membrane system is governed by sorption-selectivity properties. The two membranes with the highest selectivity, C18 (1 M) and Sil20 (α=10.1 and 6.7, respectively), were selected for more extensive testing with a feed comprising isobutanol (i) at increasing concentrations from 1% to 6% (v/v) (FIG. 3) and (ii) with the aqueous substrates and reactants from the conversion of butyric acid reaction, to simulate biofuel recovery (FIG. 4).

Example 11

Isobutanol Feed Concentration Effects

The effect of isobutanol feed concentration is an important variable in pervaporation. As the volume percent of isobutanol in the feed was increased from 1% to 6% (v/v), the flux across the membrane first decreased by an order of magnitude from ~1.0 LMH to ~0.1 LMH at <1% (v/v) and then increased to ~1.0 LMH at >4% (v/v) (FIG. 3A). The opposite behavior was observed for a (FIG. 3B). Below 1% (v/v), the flux and separation factor were similar to the high vol % cases. For the C18 grafted brush membrane, the polymer structure acts like a brush membrane. Klein and others have shown that solvent type has a large effect on the organization of brush-like structures (Klein et al., Lubrication Forces Between Surfaces Bearing Polymer Brushes, Macromolecules, 1993, 26 (21), 5552-5560; Auroy et al., Local Structure and Density Profile of Polymer Brushes, Phys. Rev. Lett., 1992, 69 (1), 93). When the solvent is "good", i.e., more apolar at higher alcohol concentrations, the brush-like structure can be maintained and the dense packing creates a membrane with high separation factor and low flux. At low alcohol concentrations, the brush-like structure collapses; there is an increase in flux, and a concomitant decrease in separation factor of the isobutanol from water. By plotting separation factor versus flux, one observes that all the membrane conditions follow a linear trend (FIG. 3C).

A novel membrane to remove isobutanol in situ from a biofuels production system must not only be able to selectively remove isobutanol, but also should retain essential reactive compounds. FIG. 1C shows the targeted immobilization reaction that requires selective removal of isobutanol using PV (Grimaldi et al., Towards Cell-Free Biofuel Production: Development of a Novel Immobilized Enzyme System, Submitted). Isobutanol must be separated from the other components that should be retained. Both the commercial PDMS membranes and the new C18 grafted brush membranes retain formate, β-nicotinamide adenine dinucleotide [reduced] (NADH), and ketoisovaleric acid; however, the novel grafted membrane retains isobutyraldehyde while the PDMS membranes do not (FIG. 4B). This achievement is critical for the successful implementation of these membranes for isobutanol recovery from the butyric acid reaction.

Additional details of our above described pervaporation experiments could be found in Grimaldi et al., New Class of Synthetic Membranes: Organophilic Pervaporation Brushes for Organics Recovery, Chem. Mater., 2015, 27, 4142-4148, with additional Supporting Information available free of charge on the ACS Publications website at DOI: 10.1021/acs.chemmater.5b01326, all of these disclosures incorporated herein by reference in their entirety.

Pervaporation Examples Conclusions

PDMS provides a pervaporation membrane that is capable of separating organic compounds from water, but this membrane cannot provide selectivity between organic compounds. Our atmospheric pressure plasma (or photo-oxidation) high throughput platform allows us to create brush and other membranes with a variety of surface chemistries (Taniguchi et al., Photo-processing and cleaning of PES and PSF Membranes, WO 03/078506; Belfort et at, UV-Assisted Grafting of PES and PSF Membranes, CA 2,422,738; Belfort et al., Genetic System And Self-Cleaving Inteins Derived Therefrom, Bioseparations And Protein Purification Employing Same, And Methods For Determining Critical, Generalizable Amino Acid Residues For Varying Intein Activity, U.S. Pat. No. 6,933,362; Belfort et al., UV-assisted grafting of PES and PSF membranes, U.S. Pat. No. 6,852,769; Belfort et al., PSF membranes, U.S. Pat. No. 6,852,769). By tuning both the chemistry and density of the grafted brush layer, one can engineer membranes with a wide range of fluxes and separation factors (Grimaldi et al., Hydrophobic Brush Membranes for Filtration Based on Solution-Diffusion Mechanism with Applications to Pervaporation (PV) & Reverse Osmosis (RO), U.S. Ser. No. 62/079,605). In addition, we were able to develop a hydrophobic membrane for a specific application that performed better than commercial PDMS membranes Graft-induced tethered polymer chains with multiple C18 alkane sidechains performed much better than the industry gold standard poly(dimethylsiloxane) membrane with selectivities of α=10.1±0.9 and 6.7±0.1, respectively, at comparable permeation fluxes of 0.7-1.0±0.1 L m$^{-2}$ h$^{-1}$.

These novel C18 membranes separated valuable alcohol products (isobutanol), while retaining and recycling other feed components. We speculate that these new hydrophobic brush membranes perform via the well-known solution-diffusion mechanism, they could also be used to separate salt from water (reverse osmosis) and fractionate gases, both of which are also based on the same mechanism. A novelty here is the use of a hydrophobic brush as a selective skin or dense layer attached to a nonselective polymeric support membrane, that is simpler to prepare and scale, and is environmentally friendly. Opportunities for further developments are many, including mixed hydrophobic brushes of different lengths, hydrophobic-hydrophilic brushes, and longer brushes.

Reverse Osmosis (RO) Examples

Example 12

General Grafted Membrane Synthesis

Microdyn-Nadir NP030 nanofiltration membranes were used as a support layer for subsequent grafting. These membranes have a poly(ether sulfone) (PES) skin which is the selective layer used mainly for 85-95% divalent ion, such as magnesium and sulfate, rejection. Monovalent ions, such as sodium and chloride, exhibit very little rejection using these membranes (<15%). The PES skin was formed by phase inversion on top of a polypropylene porous support layer used for mechanical support. These membranes were pre-soaked in ultrapure type 1 water (Milli-Q water) with a resistivity of 18.2 MΩ*cm overnight before use. After the pre-soaking procedure, the membranes were removed from the soaking container and excess water was removed using paper towels. The dried membranes were then placed in a Surfx Atomflo atmospheric pressure plasma unit to create free radicals on the light sensitive PES skin layer. The plasma irradiation settings used in experiments are the following unless otherwise stated. 10 min irradiation time, 20 mm plasma head height above sample, 30 L min$^{-1}$ helium flow rate, and 0.40 L min$^{-1}$ oxygen flow rate. After plasma treatment, the membranes were soaked in a glass vial containing hydrophobic monomer solution. The following monomers were used: methyl methacrylate (C1); ethyl methacrylate (C2); butyl methacrylate (C4); hexyl methacrylate (C6); decyl methacrylate (C10); tridecyl methacrylate (C13); and stearyl methacrylate (C18). The glass vial was then placed into an oven pre-heated to 60° C. and allowed to react for 2 h. After the reaction time period, the vial was removed from the oven and the membrane removed from the monomer solution. The membrane was rinsed with pure ethanol and then placed in 50 mL of ethanol in a centrifuge tube. The centrifuge tube was placed on an orbital shaker overnight.

The membrane was then rinsed with Milli-Q water and loaded into a high-pressure, stainless steel, dead-ended filtration cell. The stirrer speed in the cell was set at 120 rpm. The permeate outlet piping was directed into a graduated cylinder that was placed on a mass balance. The membrane was then compacted with Milli-Q water for approximately 45 min. using $N_2$ pressure at 800 psig. Volume flux measurements were taken at regular intervals to monitor the decline in flux as the membrane and pores were compressed. The water was removed and the cell was filled with a 32 g L$^{-1}$; sodium chloride in Milli-Q water solution that had been pre-filtered through a Millipore microfiltration (0.20 μm average pore size) membrane to remove undissolved solutes. The cell was again pressurized to 800 psig using $N_2$ pressure. Flux measurements were taken at regular intervals. After approximately 20-25 mL of permeate had been collected in the graduated cylinder, the pressure was vented from the cell and the permeate was transferred to a clean centrifuge tube. A conductivity probe was inserted into the centrifuge tube and a conductivity reading was recorded. This reading, in conjunction with the initial synthetic sea water conductivity, was used to calculate the observed rejection. We report observed rejection for all the monomers tested.

Figure 5:
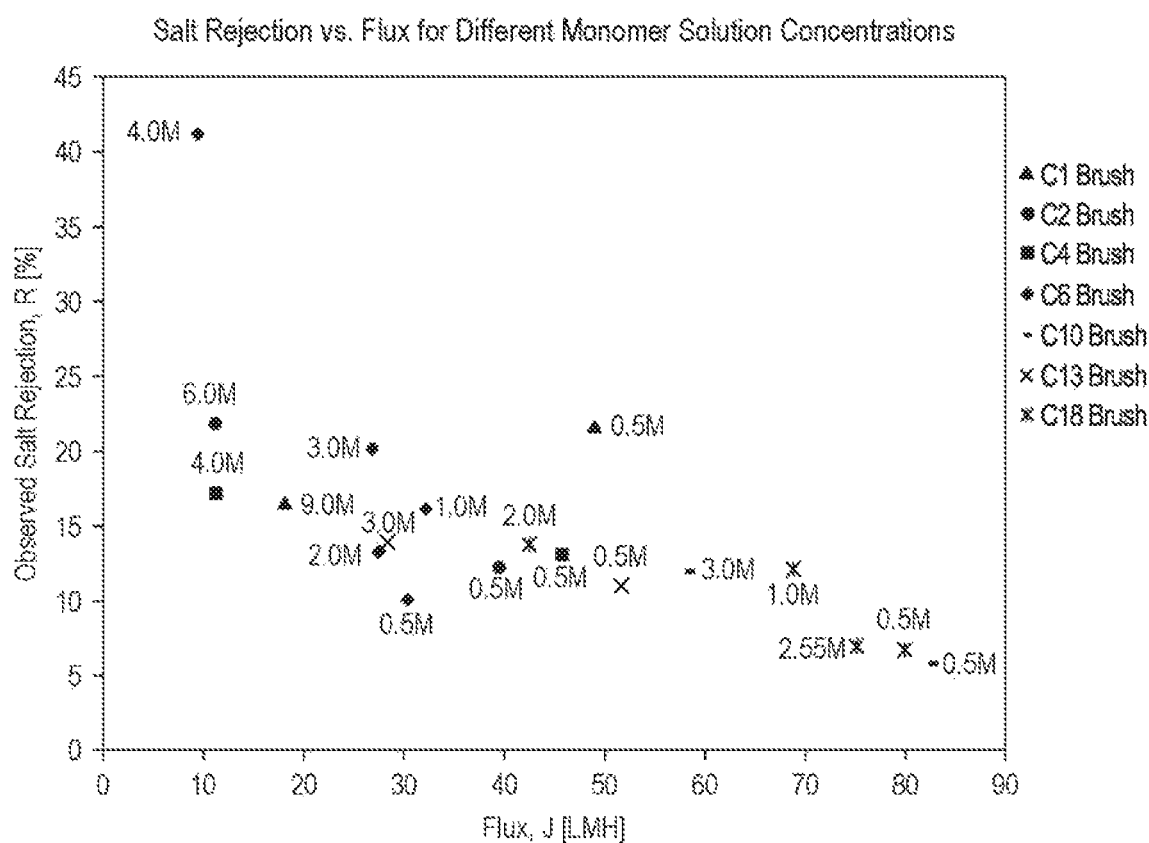
FIG. 5 shows a plot of salt rejection vs. volume flux for several hydrophobic monomers and the concentrations of their grafting solutions.

Several hydrophobic monomers were tested at several concentrations in ethanol. FIG. 5 shows a plot of observed salt rejection versus flux (in L $m^{-2}$ $h^{-1}$) for several monomers tested for desalination and their concentrations.

With reference to FIG. 5, the "CX" designation indicates that we were using a methacrylate monomer with "X" number of carbons in the alkane chain (e.g. C6 is hexyl methacrylate). We wanted to achieve both high rejection and high flux (top right of graph), but we are focusing on achieving high rejection first. The highest rejection obtained was with the C6 monomer at 4 M grafting solution concentration (top left). The baseline PES membrane (not shown) had a salt rejection of 3.7% when tested. Therefore, all of these monomers showed improved rejection of sodium chloride ions over the base PES nanofiltration membrane. All monomers tested showed desalination of synthetic seawater.

Example 13

Figure 6:
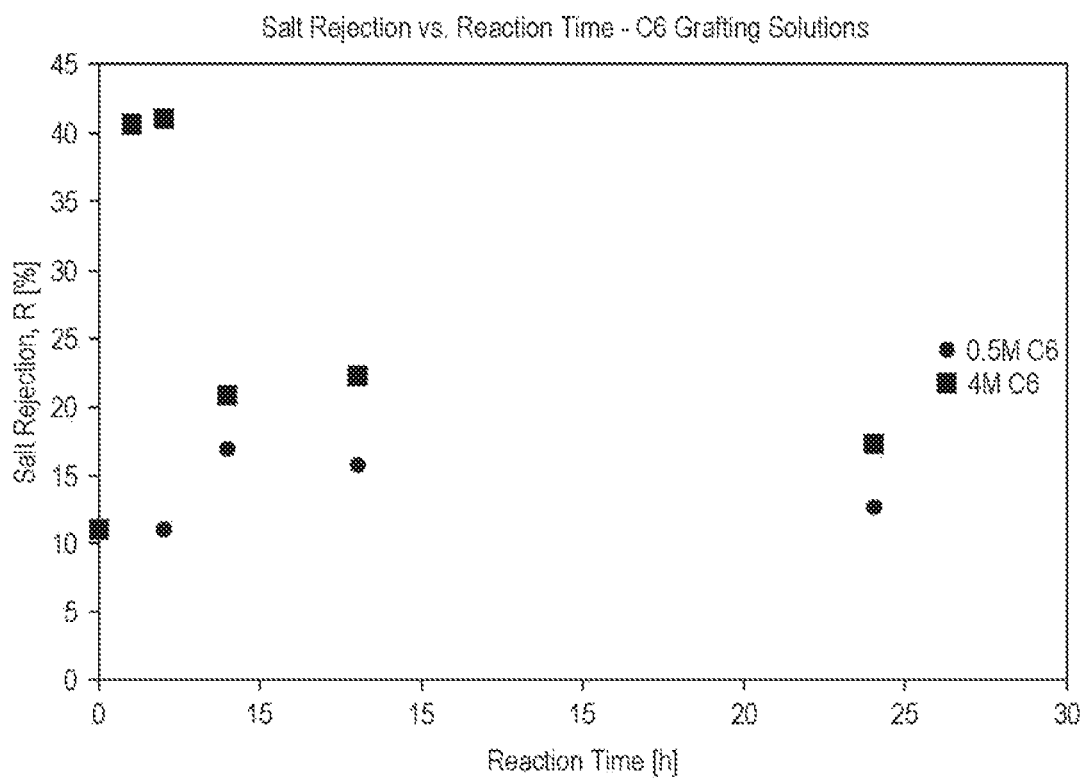
FIG. 6 shows salt rejection versus reaction time for C6 monomer grafting solutions of 0.5 M and 4 M.
Figure 7:
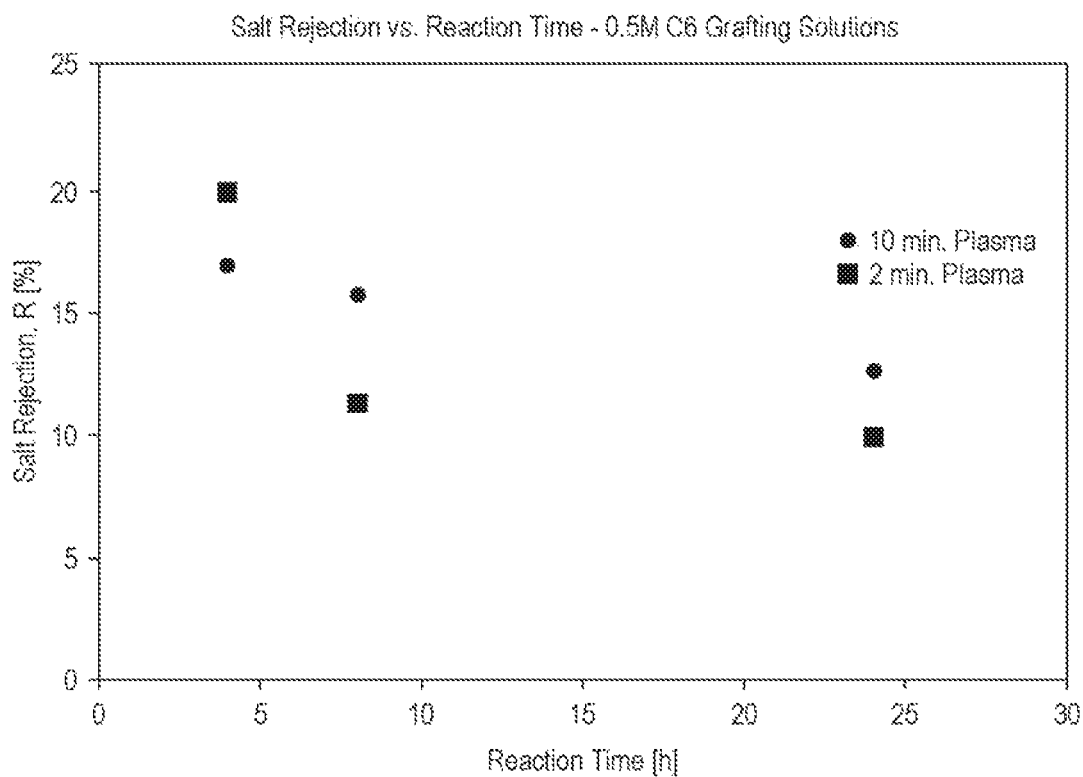
FIG. 7 shows salt rejection versus reaction time (h) for 0.5 M C6 monomer grafting solutions at 10 min and 2 min plasma treatment.

Effect of Polymerization Reaction Time and Plasma Irradiation Time on Desalination Performance The next step was to vary the reaction time of monomer solutions to determine the impact on desalination performance. The C6 monomer was chosen for this investigation. FIG. 6 shows the desalination performance with two C6 grafting solution concentrations at various reaction times (at a constant plasma irradiation time of 10 min.). After 2 h, the performance decreased. This is proposed to be due to the swelling of the polypropylene support layer, which swells in C6 solutions. FIG. 7 shows the effect of varying the plasma irradiation time on the desalination performance of 0.5 M C6 (constant concentration) grafted membranes reacted for different times. At 2 h, the performance was slightly better with the two minute irradiation time. However, at longer reaction times, again it was observed that desalination performance decreased.

Example 14

Effect of Polymer Solution Volume on Membrane Support Swelling

Instead of soaking the membrane in a vial full of a polymer mixture, we sandwiched the membrane between two glass plates and an O-ring and clamped them together before placing it in the oven. This led to a ~0.90% reduction in volume needed to graft onto the membrane surface. We have proven this method works just as well as the membrane modified in the glass vial for a 4 M C6 solution at 2 hours reaction time based on desalination performance.

Example 15

Reverse Osmosis Examples Conclusions

Current desalination membranes are synthesized using complex methods, such as interfacial polymerization. Our atmospheric pressure plasma (or photo-oxidation) platform allows us to create brush and other membranes with a variety of surface chemistries (Taniguchi et al., Photo-processing and cleaning of PES and PSF Membranes, WO 03/078506, Belfort et al., UV-Assisted Grafting of PES and PSF Membranes, CA 2,422,738; Belfort et al., Genetic System And Self-Cleaving Inteins Derived Therefrom, Bioseparations And Protein Purification Employing Same, And Methods For Determining Critical, Generalizable Amino Acid Residues For Varying Intein Activity, U.S. Pat. No. 6,933,362; Belfort et al., UV-assisted grafting of PES and PSF membranes, U.S. Pat. No. 6,852,769; Belfort et al., PSF membranes, U.S. Pat. No. 6,852,769). By tuning both the chemistry and density of the grafted brush layer, one can engineer membranes with a wide range of fluxes and separation factors (Grimaldi et al., Hydrophobic Brush Membranes for Filtration Based on Solution-Diffusion Mechanism with Applications to Pervaporation (PV) & Reverse Osmosis (RO), U.S. Ser. No. 62/079,605). In addition, we were able to develop a hydrophobic membrane for desalination, which is unlike the hydrophilic membranes used today. Graft-induced tethered polymer chains with multiple C6 alkane sidechains performed the best from our screening results and were able to achieve 42% desalination without optimization.

These novel C6 membranes separated water from salt ions. We speculate that these new hydrophobic brush membranes perform via the well-known solution-diffusion mechanism. A novelty here is the use of a hydrophobic brush as a selective skin or dense layer attached to a non-selective polymeric support membrane, that is simpler to prepare and scale, and is environmentally friendly. The major advantage to hydrophobic membranes, based on theory, is that there should be nearly frictionless flow through them due to the inability of the water to hydrogen bond with the brushes or pore walls. Since our modified brush membranes can be synthesized from existing nanofiltration (NF) support membranes, they are much more economical. Opportunities for further developments are many, including mixed hydrophobic brushes of different lengths, hydrophobic-hydrophilic brushes, and longer brushes.

Example 16

Gas Fractionation

Polymer based membranes find wide use in gas separations systems such as the recovery of hydrogen from carbon dioxide or carbon monoxide. When using our synthetic membranes for gas separation (i.e., gas fractionation), hydrogen, $CO_2$, and other impurities will enter via a feed stream. In this case, gas will be supplied to the first hydrophobic synthetic brush membrane (i.e., our synthetic membrane, which can be prepared, for example, as disclosed in Example 2 or Example 12 above) at a pressure of 50-200 atm and a flow rate of 1,000-3,000 standard cubic feet per minute (SCFM). The permeate from this first membrane will be kept at a pressure of 20-100 atm. The permeate from this first membrane will be recycled back to the reactor and will be enriched in hydrogen gas. The feed to the second hydrophobic synthetic brush membrane (i.e., our synthetic membrane, which can be prepared, for example, as disclosed in Example 2 or Example 12 above) will be supplied at 50-200 atm. The permeate from the second membrane will be kept at a pressure of 10-50 atm. The permeate from the second membrane will also be recycled back to the reactor and will be further enriched in hydrogen gas. The second membrane will have a higher pressure ratio to ensure there will be a high enough hydrogen concentration in the permeate to be recycled back to the reactor. In summary, relatively pure hydrogen gas is recovered at high concentrations from a feed mixture of hydrogen and carbon dioxide or carbon monoxide.

While only certain features of the invention have been illustrated and described herein, many modifications and changes will occur to those skilled in the art. It is, therefore, to be understood that the appended claims are intended to cover all such modifications and changes as falling within the true spirit of the invention.

Throughout this application, various references are referred to. The disclosures of these publications in their entireties are hereby incorporated by reference as if written herein.

What is claimed is:

1. A method of making a synthetic membrane for recovering a target via separation, the method comprising:
    contacting an initiator with a surface of a polymeric membrane support layer;
    irradiating the surface of the polymeric membrane support layer; and
    contacting a monomer solution with the surface of the polymeric membrane support layer, the monomer solution comprising vinyl monomers and a solvent.

2. The method according to claim 1, wherein the polymeric membrane support layer includes polysulfone, cellulose, cellulose acetate, polyvinylidene fluoride, polyimide, polyethylene, polypropylene, polyacrylonitrile, and polyethylene terephthalate.

3. The method according to claim 1, wherein the initiator includes benzophenone, di-tert-butyl peroxide, dibenzoyl peroxide, methyl ethyl ketone peroxide, acetone peroxide, peroxydisulfate salts, azobisisobutyronitrile, 1,1'-Azobis(cyclohexanecarbonitrile) (ABCN), or combinations thereof.

4. The method according to claim 1 wherein the vinyl monomers are $C_{1-20}$ alkyl methacrylate monomers, polyethylene glycol monomers, styrene monomers, or combinations thereof.

5. The method according to claim 1, wherein the vinyl monomers are $C_{18}$ alkyl methacrylate monomers.

6. The method according to claim 1, wherein the vinyl monomers are $C_6$ alkyl methacrylate monomers.

7. The method according to claim 1, wherein a molar concentration of the vinyl monomers in the monomer solution is from about 0.01 M to about 9.0 M.

8. The method according to claim 1, wherein irradiating the surface of the polymeric membrane support layer includes:
    exposing the surface of the polymeric membrane support layer to atmospheric pressure plasma for a time period of from about 2 minutes to about 10 minutes.

9. The method according to claim 1, wherein irradiating the surface of the polymeric membrane support layer includes:
    exposing the surface of the polymeric membrane support layer to ultraviolet light for a time period of from about 10 seconds to about 5 minutes.

* * * * *